(12) United States Patent
Griffiths (10) Patent No.: US 8,342,840 B2
(45) Date of Patent: Jan. 1, 2013

(54) DENTAL RETAINER HAVING IMPROVED JOINT

(76) Inventor: Paul William Griffiths, Dorval (CA)

(*) Notice: Subject to any disclaimer, the term of this patent is extended or adjusted under 35 U.S.C. 154(b) by 0 days.

(21) Appl. No.: 13/092,788

(22) Filed: Apr. 22, 2011

(65) Prior Publication Data

US 2011/0195370 A1    Aug. 11, 2011

Related U.S. Application Data

(63) Continuation of application No. PCT/IB2009/054687, filed on Oct. 22, 2009.

(60) Provisional application No. 61/107,415, filed on Oct. 22, 2008.

(51) Int. Cl.
*A61C 7/08* (2006.01)
(52) U.S. Cl. ............................... 433/18; 433/6
(58) Field of Classification Search .................. 433/5, 6, 433/18, 24
See application file for complete search history.

(56) References Cited

U.S. PATENT DOCUMENTS

| 2,983,046 | A | * | 5/1961 | Jenkins | 128/861 |
| 4,224,021 | A | * | 9/1980 | Foxman | 433/2 |
| 4,708,646 | A | * | 11/1987 | Jasper | 433/19 |
| 5,087,196 | A | * | 2/1992 | Polanco | 433/21 |
| 5,897,313 | A | * | 4/1999 | Cleary et al. | 433/19 |
| 6,332,774 | B1 | * | 12/2001 | Chikami | 433/20 |
| 7,037,107 | B2 | * | 5/2006 | Yamamoto | 433/20 |
| 2001/0047573 | A1 | * | 12/2001 | Anderson | 24/300 |
| 2006/0257813 | A1 | * | 11/2006 | Highland | 433/21 |

* cited by examiner

*Primary Examiner* — Ralph Lewis
(74) *Attorney, Agent, or Firm* — McNeely, Hare & War, LLP; William D. Hare, Esq.

(57) ABSTRACT

The invention relates to a dentition retaining apparatus that includes a joint between a holding member and a supporting member. The holding member is elastically deformable and terminates in an end segment having a length with an outer diameter. The joint includes a coil extending from the supporting member and having an inner diameter that is less than the outer diameter of the end segment of the holding member. The coil is placed around at least a portion of the end segment of the holding member. The coil compresses the end segment of the holding member.

28 Claims, 6 Drawing Sheets

Prior Art

DENTAL RETAINER HAVING IMPROVED JOINT

CROSS-REFERENCE TO RELATED APPLICATIONS

This application is a continuation application of and claims priority to PCT/IB2009/054687 filed Oct. 22, 2009, which claims priority from U.S. Provisional Patent Application No. 61/107,415, filed on Oct. 22, 2008. The contents of both are incorporated herein in their entirety by reference.

TECHNICAL FIELD

The field of the invention generally relates to a dental retainer coil spring joint that holds a plastic labial bow of an orthodontic dental retainer.

BACKGROUND

Dental braces or retainers are used in orthodontics to align teeth and their position with regard to a person's bite. They are often used to correct malocclusions such as underbites, overbites, cross bites and open bites, or crooked teeth and various other flaws of teeth and jaws, whether cosmetic or structural. Dental retainers are often used in conjunction with other orthodontic appliances to widen the palate or jaws or otherwise shape the teeth and jaws. U.S. Pat. No. 6,332,774 to Chikami is directed to retainers that include a holding member and a supporting member or wire with the wire is positioned within the holding portion. The wire is retained within the holding member by a clasp type component.

U.S. Pat. No. 6,053,730 to Cleary is directed to an orthodontic force module for correcting Class II malocclusions and includes a resilient body and a coupling connected to the body for connecting the body to a selected orthodontic appliance located on the patient's upper jaw. The coupling includes an opening that extends in a reference plane substantially parallel to and preferably containing the longitudinal axis of the body. According to Cleary, the orientation of the opening provides freedom of movement of the force module when the patient's jaws are opened or closed and reduces the likelihood of fracture of the coupling. FIG. 11 of Cleary shows a coil or spring 23e placed within a sheath 38e or the sheath 38e injection molded around it.

U.S. Pat. No. 5,897,313 to Cleary et al. is directed to a force module for moving individual malpositioned teeth or entire dental arches during orthodontic therapy. The module includes an elongated body with couplings at each end of the body for connection to selected orthodontic appliances. The module also includes couplings that have a sleeve portion for receiving end sections of the body and an arm portion connected to each sleeve portion, and the arm portions extend at an obtuse angle relative to the longitudinal axis of the body. FIG. 12 of Cleary shows a force module 510 that is encased at opposite ends in couplers 524, 526. Cleary et al. describes the couplers as being fixed to the force module using a variety of means, such as swaging, pinning, staking, or adhering with an adhesive.

U.S. Pat. No. 4,976,614 to Tepper is directed to a removable orthodontic appliance that is seated on the teeth on each side at a midregion by clasps which provide a base for a label filament serving as a reference arch, and curved lingual spring filament which urges the teeth against the reference. The mountings for the filaments comprise open loops having filament receiving sleeves at each end by means of which the positions and angles of the filaments may be adjusted but the filaments may be coupled in solely by mechanical means. A retainer device may use synthetic resin filaments of transparent material to hold the teeth against relapse. The figures disclose clasps formed as tubes that encase the metal wire of the appliance. Tepper should not be an obstacle to obtaining a patent as it does not describe or suggest a coil or spring used to connect a polymer labial bow to a dental retainer by encircling the outer surface of the labial bow.

U.S. Pat. No. 4,875,856 to Grussmark is directed to an orthodontic appliance for closing spaces between two adjacent teeth. The device disclosed includes a bar of elastomeric material or an elastic element and ligature wire means or an inelastic element for securing the bar in place over the labial or buccal or lingual faces of the teeth. The ligature wire means includes ligature wire secured to one or both ends of the bar for mounting and tensioning of the elastomeric bar on adjacent teeth. Grussmark discloses the end of the ligature wire as being coiled around itself to secure the wire in place.

U.S. Pat. No. 4,676,745 to Zurita is directed to an orthodontic appliance to provide normal alignment of the teeth. The orthodontic appliance includes a U-shaped band of flexible material having a pair of rearwardly extending arms where the U-shaped band conforms to the labial surface of the dental arch when in position in the mouth. It also includes a pair of anchors each of which is adapted to cooperate with a molar on opposite sides of the mouth to maintain the U-shaped band in position against the labial surface of the dental arch. The orthodontic appliance further includes a resilient member joining the anchors to the arms of the U-shaped band with the resilient member applying a biasing force to the labial surface of the dental arch through the U-shaped band. FIG. 3 of Zurita discloses elongated slide members 22 with protrusions 34 into which arms 14/42 are inserted to mount the U-shaped band to the slide members 22.

U.S. Pat. No. 4,059,900 to Orthwein discloses a removable dental restoration for filling an edentulous space defined at each end by a natural tooth, the restoration having at each end a means for resiliently gripping the adjacent natural tooth. In a first embodiment, the gripping means is releasable by application of opposing forces to the longitudinal side walls of the restoration. A second embodiment has the gripping means releasable by applying a simultaneous force to the end wall of each respective gripping means. Further embodiments also have gripping means releasable by application of opposing forces to the longitudinal side walls of the restoration, but the gripping means are formed separately from and attachable to the restoration. Orthwein discloses clasps and gripping means in his FIGS. 16-18.

U.S. Pat. No. 4,224,021 to Foxman discloses an adjustable attachment for a labial arch retainer. The retainer is of the type having a palatal section configured to conform to the roof of the mouth of a patient, a pair of extension wires extending anteriorally from the palatal section, an attachment hook provided at the terminal end of each extension wire, and a resilient synthetic band adapted to exert pressure against the teeth of the patient. The adjustable attachment is connected between the resilient band and the attachment hook in a manner which permits the length of the resilient band to be varied thereby permitting adjustment of the pressure exerted against the teeth of the patient. FIGS. 1 and 2 of Foxman show a connector 9 for connecting to a band 3. The connector includes arms 17/18 that fold over the band.

The disclosure of the above prior art references is incorporated herein in their entirety by reference.

SUMMARY

In one general aspect, a dentition retaining apparatus includes a joint between a holding member, such as a labial bow, and a supporting member, such as a metal wire with a coiled end. The holding member is elastically deformable and terminates in an end segment having a length with an outer diameter. The joint includes a coil extending from the supporting member and having an inner diameter that is less than the outer diameter of the end segment of the holding member. The coil is placed around at least a portion of the end segment of the holding member. The coil compresses or is compressed against the end segment of the holding member.

Embodiments of the dentition retaining apparatus may include one or more of the following features. For example, the coil may have at least approximately one-half of a revolution. The coil may have between approximately one-half of a revolution and thirty revolutions, or between approximately two revolutions and ten revolutions. The coil may have between approximately one-half of a revolution and three revolutions. The coil may have approximately one and one-half revolutions.

The inner diameter of the coil may be less than the outer diameter of the end segment of the holding member prior to placing the coil around the end segment. The inner diameter of the coil may be greater than the outer diameter of the end segment of the holding member prior to placing the coil around the end segment. The inner diameter of the coil may be less than the outer diameter of the end segment of the holding member after placing the coil around the end segment.

The coil may have a pitch angle of between approximately 15 degrees and approximately 90 degrees. The coil may have a pitch angle between approximately 40 degrees and 50 degrees.

The coil may have a spacing of between approximately 0 mm and 25 mm The coil may have a spacing of between approximately 0 mm and 3 mm.

The coil may be made of a wire having an outer diameter of between approximately 0.5 mm and approximately 3 mm The wire may have an outer diameter of between approximately 0.7 mm and approximately 1.5 mm.

The joint may have a length of between approximately 1 mm and 10 mm. The length of the joint may be between approximately 4 mm and 8 mm.

The supporting member may be a metal or polymer material. The dentition retaining apparatus may include one or more of a retainer and a labial bow. The joint of the dentition retaining apparatus may be able to hold a static weight of more than about 9 kg to at least about 13 kg.

In another general aspect there is provided a process for forming a dentition retaining apparatus. The process includes
a) providing a holding member, the holding member being elastically deformable and terminating in an end segment having a length with an outer diameter;
b) providing a supporting member having a coil extending from the supporting member, the coil having an inner diameter that is less than the outer diameter of the end segment of the holding member; and
c) placing the coil around at least a portion of the end segment of the holding member to form a joint between the holding member and the supporting member, whereby the coil compresses the end segment of the holding member.

Embodiments of the method may include one or more of the features described above or herein. For example, the coil may be compressed against the end segment of the holding member when the inner diameter of the coil is greater than the outer diameter of the end segment.

In another general aspect there is provided a method for correcting the orientation of teeth. The method includes providing a dentition retaining apparatus comprising a joint between a holding member and a supporting member, the holding member being elastically deformable and terminating in an end segment having a length with an outer diameter, the joint comprising a coil extending from the supporting member and having an inner diameter that is less than the outer diameter of the end segment of the holding member and being placed around at least a portion of the end segment of the holding member whereby the coil compresses or is compressed against the end segment of the holding member.

Embodiments of the method may include one or more of the features described above or herein. For example, the coil may have between approximately one-half of a revolution and thirty revolutions. The coil may be crimped or compressed against the end segment of the holding member when the inner diameter of the coil is greater than the outer diameter of the end segment.

The details of various embodiments of the invention are set forth in the accompanying drawings and the description below. Other features and advantages of the invention will be apparent from the description, the drawings, and the claims.

In another general aspect, the invention includes a labial bow that includes a clear holding member and a supporting member. The clear holding member is configured to be positioned against the front teeth of a patient. The holding member is elastically deformable and has a middle portion with at least one flat surface and two side portions extending from the middle portions. The side portions are generally tubular in shape and have an outer diameter. The holding member is formed of a highly oriented polymer.

The supporting member is configured to be positioned against the side teeth of a patient and is formed of a metal and terminates in a coil at one end with the coil having an inner diameter that is less than the outer diameter of the end segment of the holding member. The coil is positioned around at least a portion of the end segment of the holding member whereby the coil compresses or is compressed against the end segment of the holding member to form a joint between the holding member and the supporting member.

Embodiments of the labial bow may include one or more of the features described above or herein. For example, the labial bow may be mounted to a dental retainer arch to form a dental retainer.

DETAILED DESCRIPTION

Most orthodontic retainers use a stainless steel wire as a holding member to control the position of the upper and lower front teeth. Placing the stainless steel in such a prominent view is undesirable to many patients. Instead of a stainless steel wire, some orthodontic retainers use a polymer instead. The polymer holding member then is joined to a wire supporting member that extends to the back of the teeth. Use of a polymer holding member, however, creates its own problems, such as breakage at the joint formed by the polymer holding member and the metal wire supporting member.

The inventor has developed a new joint for use in dental devices, including dentition devices such are retainers and labial bows. The joint involves a coil connected to, extending from or a part of a first member, the coil being placed around a second member having elastic properties such that the coil slightly embeds itself in the second member. When placed around the second member, the coil may have an inner diameter that is the same as or less than the outer diameter of the second member that it encircles. In another embodiment, the coil has an outer diameter that is the same as or greater than the outer diameter of the second member that it encircles. In this embodiment, the coil is placed around the second member and crimped or otherwise compressed onto the second member. Without being limited by theory, the inventor believes that in either embodiment, attempting to pull the joint off of the second member will create resistance as the coil embeds itself into the second member.

Figure 1:
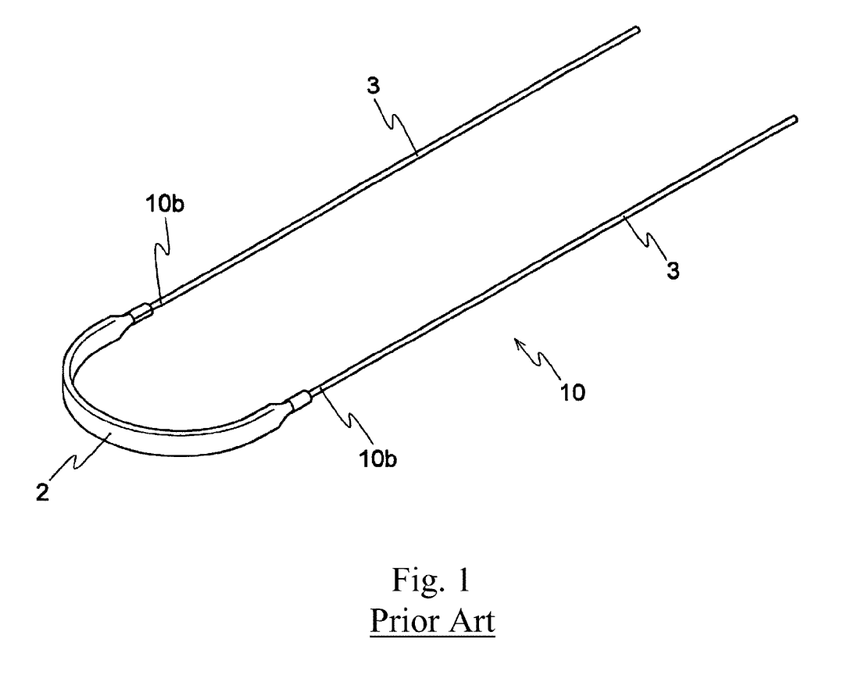
FIG. 1 is a perspective view of a component of a holding member and supporting member of a dental retainer with the supporting member retained within the holding member by a clasp.
Figure 2:
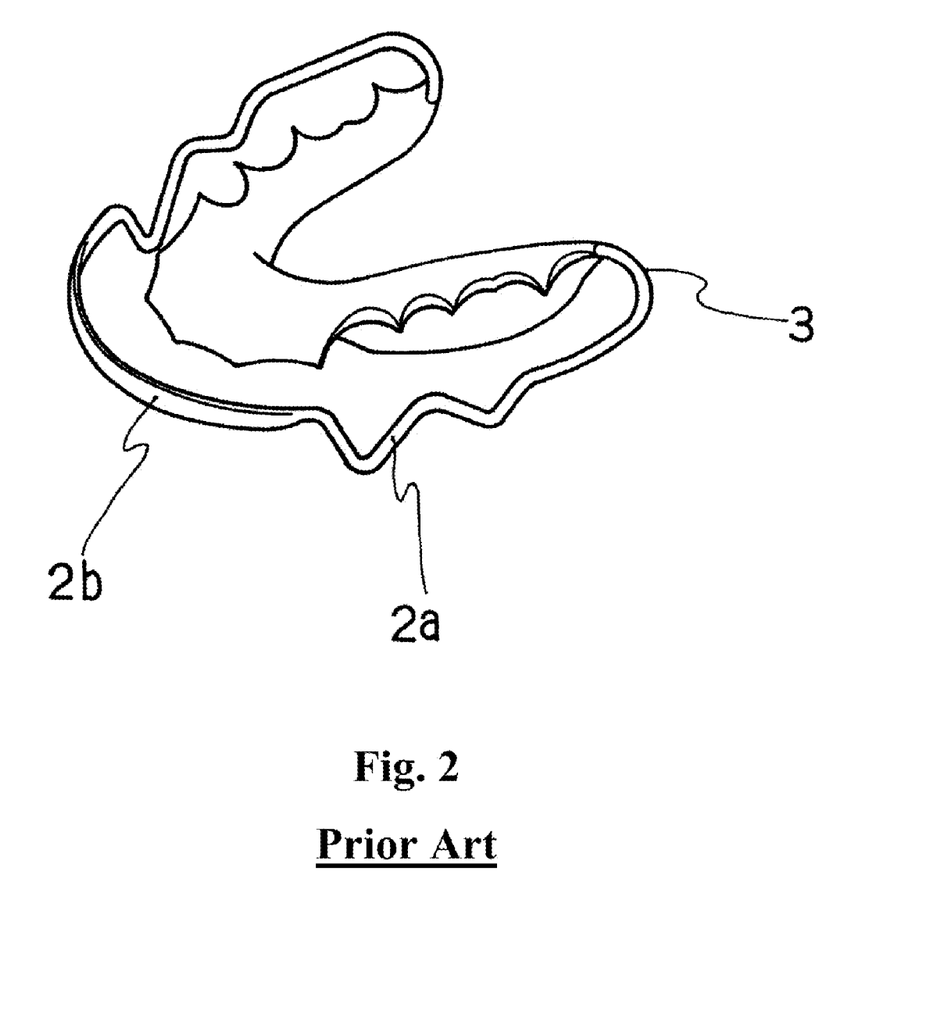
FIG. 2 is a perspective view of the component of FIG. 1 used in a dental retainer.

FIG. 1 shows a component 10 of a dental retainer in which a portion 10*b* of the metal wire 3 is inserted within the holding member 2 and a clasp (unnumbered) is secured around the holding member 2 where the metal wire 3 enters. In use, the holding member 2 is pressed against the front teeth and the supporting member 3 generally passes around the outside of the side teeth. FIG. 2 shows the component 10 used with a completed dental retainer. In use, the front teeth are pressed against the holding member 2*b* and the wire 3 is bent at one end 2*a* to conform to the teeth against which it is placed. The holding member 2*b* receives the end of the wire 3 and is held in place with, for example, the clasp illustrated in FIG. 1.

Referring to FIGS. 3-7, a dentition apparatus 100 includes a holding member or first member 105 and a supporting member or second member 110. The second member has an end portion 115 that extends from the second member or is at a terminal end of the second member. The end portion 115 has an outer diameter and has elastic characteristics. The second member optionally has the same elastic characteristics as the end portion. The second member may be a labial bow or a retainer. If the second member is a labial bow, the end portion may be at one end of the labial bow and a second end portion may be at the opposite end of the labial bow. If the second member is a retainer, the end portion may be any portion of the retainer that forms a connection with a supporting member or wire.

The first member includes a coil 120 that extends from an end of the first member and encircles at least a portion of the end portion 115 of the second member 110. The coil 120 is made of a wire and constructed according to various properties, including choice of materials, dimensions of the wire, pitch of the coil, number of revolutions of the coil, distance between revolutions of the coil, inner diameter formed by the coil, etc.

The materials that may be used to make the wire that forms the coil include metals, polymers, and combinations of the two. Examples of metals include stainless steel, nickel titanium and other biocompatible metals. Examples of plastics include polyethylene terephthalate, nylon, polyethylene, polypropylene, polyurethane, and other biocompatible plastics. In general, the wire that forms the coil should have sufficient tensile strength to prevent the wire from being plastically deformed when tension is applied to the coil. The labial bow may be made of plastics such as polyethylene terephthalate, nylon, polyethylene, polypropylene, polyurethane, and other biocompatible plastics. The plastic may be extruded as a rod, and then oriented and flattened to make the labial bow.

The outer diameter of the wire used to make the coil can range from approximately 0.5 mm and 3.0 mm in diameter. More particularly, the wire may have an outer diameter of between approximately 0.7 mm and approximately 1.5 mm, and even more particularly approximately 0.9 mm or 1.0 mm.

Figure 3:
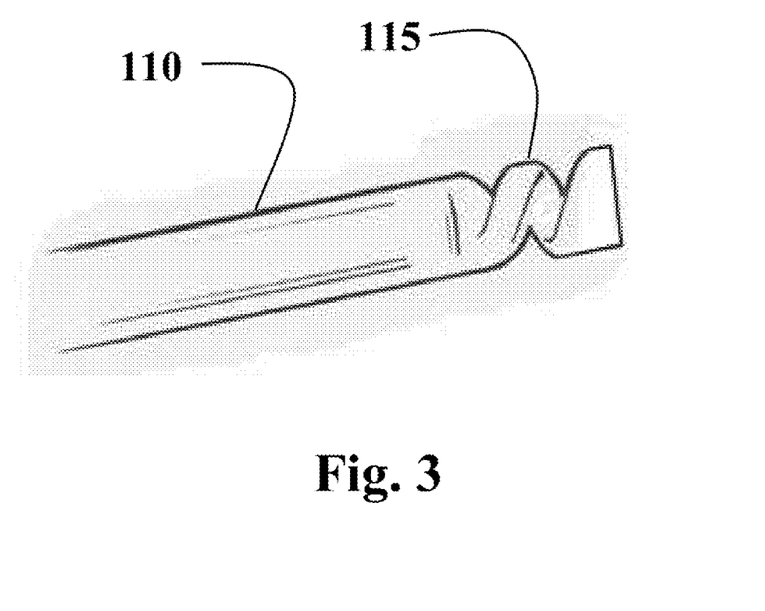
FIG. 3 is a perspective view of a holding member or labial bow used in a dental retainer.

The joint is formed from the coil and the coil may be at least approximately one-half of a revolution to form the joint. In some implementations, the coil formed by between approximately one-half of a revolution and thirty revolutions, between approximately two and ten revolutions, between approximately one-half of a revolution and three revolutions and, more particularly, approximately one and one-half revolutions. FIG. 3 illustrates an indicator 130 for the measurement of one revolution of the coil.

The inner diameter of the coil generally is the same as or less than the outer diameter of the end segment of the holding member prior to placing the coil around the end segment. In another implementation, the inner diameter of the coil is the same as or less than the outer diameter of the end segment of the holding member after placing the coil around the end segment. In yet another implementation, the inner diameter of the coil is the same as or greater than the outer diameter of the end segment of the holding member. In this implementation, the coil is placed over the end segment and then crimped or compressed around the end segment. In this manner, the coil is in compression against the end segment.

The coil has a pitch angle 125 between approximately 15 degrees and approximately 90 degrees. In some implementation, the coil has a pitch angle between approximately 40 degrees and 50 degrees. The pitch angle is measured relative to a line formed by the end portion around which the coil is placed.

The coil has a spacing of between approximately 0 mm and 25 mm but may be implemented at a spacing of between approximately 0 mm and 3 mm.

Further, the coil forms a joint that has a particular range of lengths. In most cases, the joint has a length of between approximately 1 mm and 10 mm but may be implemented at a length of between approximately 4 mm and 8 mm.

To make the dental retaining device, the holding member is formed or provided in which the holding member terminates in an end segment having a length with an outer diameter. The supporting member having a coil extending from the supporting member also is provided. In one embodiment, the coil has an inner diameter that is less than the outer diameter of the end segment of the holding member. Then the coil is placed around at least a portion of the end segment of the holding member to form a joint between the holding member and the supporting member. In forming this joint, the coil compresses the end segment of the holding member. In another embodiment, the coil has an inner diameter that is the same as or greater than the outer diameter of the end segment of the holding member. The coil is placed around at least a portion of the end segment of the holding member to form a joint between the holding member and the supporting member. In forming this joint, the coil is crimped or compressed around the end segment of the holding member. The holding member, supporting member and coil have the features described above.

Figure 4:
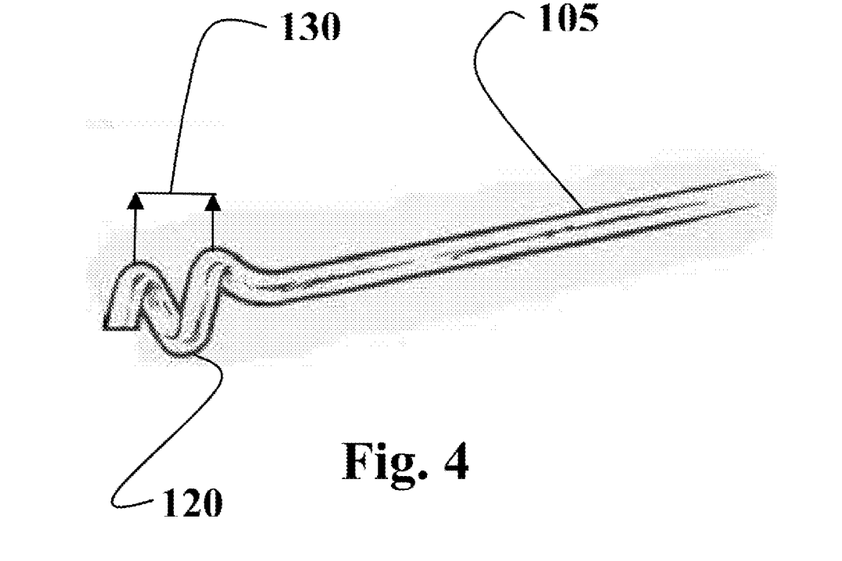
FIG. 4 is a perspective view of a supporting member used in a dental retainer.
Figure 5:
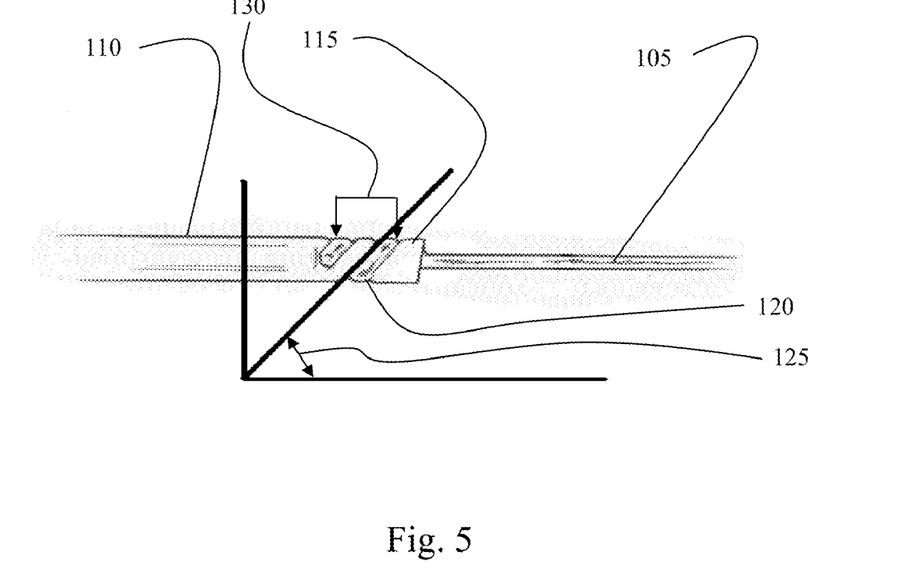
FIG. 5 is a perspective view of the coil of the supporting member of FIG. 4 placed around an end portion of the holding member of FIG. 3 to form a joint between the supporting member and the holding member.
Figure 6:
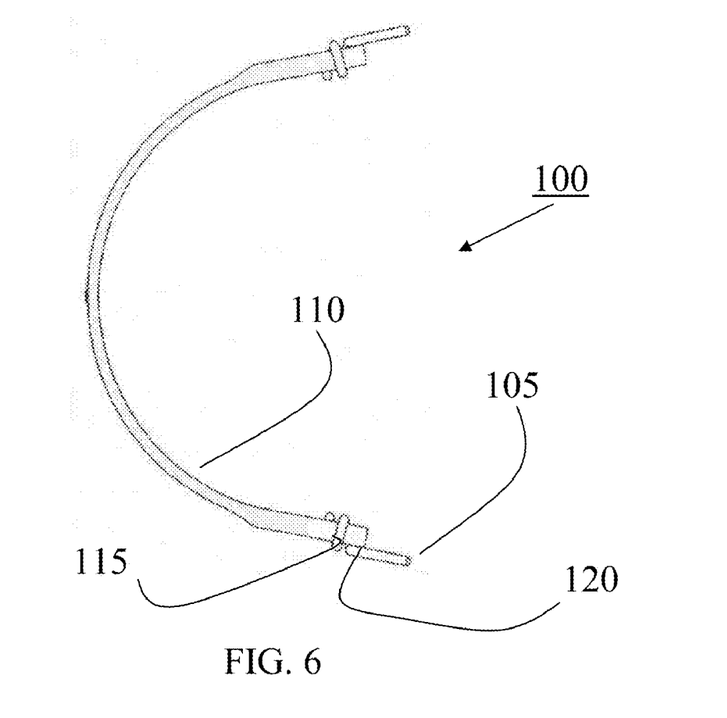
FIG. 6 is a top view of a dentition retainer using the joint of FIG. 5
Figure 7:
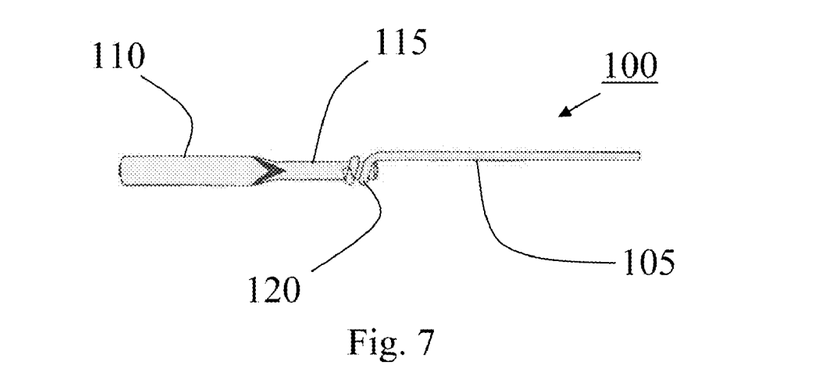
FIG. 7 is a side view of the dentition retainer of FIG. 6.

In another aspect, as the coil is crushed into the extension of the polymer material, the extension deforms to the point where it takes on the form of the coil that is embedding into it. This aspect is seen in FIGS. 3 and 4. This unique intertwining of the plastic shape with the wire coil gives it its unique holding ability which is completely different from anything on the market today. The resistance to disconnection of the plastic and the metal coil spring in a linear fashion (refer to FIG. 5) requires a great deal of force. In this design there is no clamping action it is an intertwining of plastic and metal. In contrast, Foxman's design (described above) is dependent on the strength of the clamping ability where the metal clamps against the plastic. In the inventor's experience, the problem with clamping metal around the plastic is as soon as the metal fatigues its clamping system weakens and the joint fails. This technique does not hold up during the long term. For example, this was seen with respect to the prior art disclosed herein from Chikami.

In a method of using the joint described herein, a patient uses a dentition retaining apparatus that includes the coil-type joint between the holding member and the supporting member. As described above, the holding member is elastically deformable and terminates in an end segment having a length with an outer diameter. The joint includes the coil extending from the supporting member and having an inner diameter that may be less than or greater than the outer diameter of the end segment of the holding member. The joint is placed around at least a portion of the end segment of the holding member such that the coil compresses the end segment of the holding member, or is crimped onto the end segment such that the coil compresses the end segment of the holding member. The holding member, supporting member and coil have the features described above.

The joint has been tested for its ability to retain the coil to the holding member. For a joint in which the coil was of approximately 3 mm diameter, a pitch angle of approximately 70 degrees, and had approximately 1.5 revolutions around the holding member, the joint was able to hold a static weight of at least 30.5 lbs or 13.8 kg. Thus, it is anticipated that the joint will be able to hold a static weight of at least about 30.5 lbs or 13.8 kg, or between about at least 9 kg and 13.8 kg, and more broadly between about at least 3 kg and about 13.8 kg. This is an advantageous increase in joint strength in comparison to both the prior art and U.S. Pat. No. 6,332,774 to Chikami Chikami describes the extractive strength of the wire member from the holding portion of the prior art as being about 3.0 kg and claims that the extractive strength of his system is about 9.0 kg. Thus, the joint described above had an increase in strength of approximately 50% compared to Chikami.

Example

Figure 8:
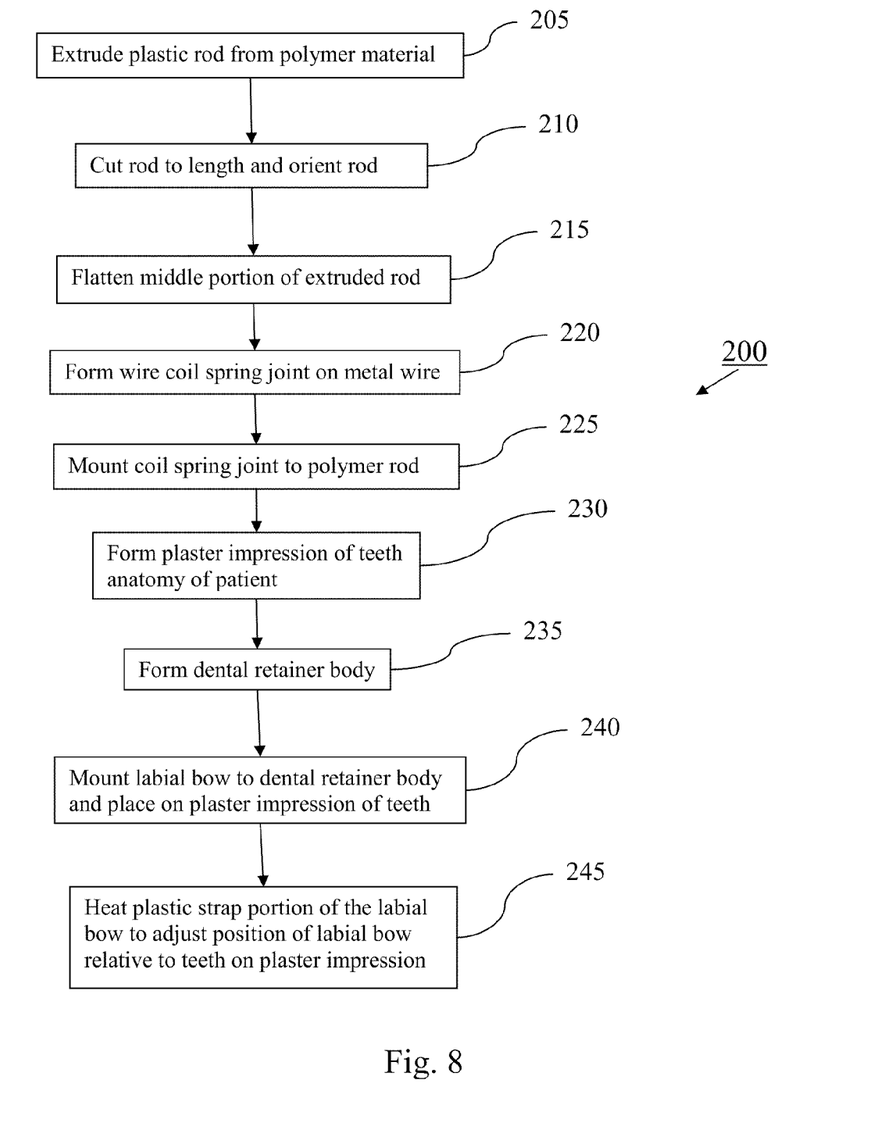
FIG. 8 is a flow chart illustrating the process for forming a dental retainer.

Referring to FIG. 8, a process 200 for forming a dental retainer includes forming a plastic strap, attaching the plastic strap to a metal coil joint to form a labial bow, forming a dental retainer, attaching the labial bow to the dental retainer and customizing the fit of the labial bow to an individual patient's dental anatomy.

Formation of the Polymer Bow

In one experiment, three different sources of polyethylene terephthalate were used, each source being from a different manufacturer. It was noted that there were differences in color and stiffness between the polymers of different sources. It was found that all three of the polymers had similar abilities to shrink when heated in the final assembly.

The polymer was extruded into a rod shape (step 205) and either air or water cooled depending which properties were to be imparted into the plastic. Brittleness and crystallization were found to be impacted by cooling time of the extruded rod. When desired to impart orientation to the polymer, the cooled rod was reheated and stretched to orient the polymer rod. This allows the polymer to be suitable for having a shrink memory imparted. It was found that polyethylene terephthalate can be highly oriented by heating and stretching. This was useful based on the understanding that the more a plastic is oriented, the more it tends to shrink when heated. The rod was worked to achieve an oriented rod that is approximately 1.75 mm in diameter (step 210). Although the rod had outer diameter of 1.75 mm, other diameters are expected to be useful, for example over a range of 1.5 to 2.0 mm or 1.25 to 2.5 mm. The outer diameter is selected such that the further processing of the rod will provide a labial bow of the desired dimensions.

The oriented rod is then placed in a heated mold at a temperature ranging from approximately 160-230 degrees Celsius. The rod then is stamped into a "U" flattened shape that is approximately 0.8 mm in thickness and 3 mm in width (step 215). The "U" shape is of a curve or radius that is approximately that of an average dental arch.

Attachment of the Bow to Coil Springs

With the polymer portion of the labial bow formed, the coil spring joint next is formed (step 220) and attached to the round extensions on each side of the flattened plastic section by means of a pressing machine (step 225). For example, the coil spring can be formed of a 0.9 mm stainless steel wire, or a wire of a range of 0.8 to 1.0 mm in diameter. This configuration of the coil spring joint attached to the round extensions of the labial bow is seen best in FIG. 6. The joint can be attached anywhere along the round part of the extension but the inventor has found good results when placed at the end of the flattened section. The inventor has also found that the joint can be placed approximately 8-10 mm away from the end of the plastic extension. The distance can be adjusted based on the size of the mouth.

The final product is a "U" shape polyethylene terephthalate rod that is flattened in the middle with two coil springs attached at each end of the approximately 2 inch extensions with the wire extending off the coil spring joint. The wire may be 0.036 inches or 0.9 mm in diameter.

Formation of an Orthodontic Retainer

A plaster mold is made of a mouth of a patient who has just finished an orthodontic treatment in which orthodontic brackets were used to align the teeth (step 230). The teeth of such a patient must be held in place for a period of time after the orthodontic brackets have been removed from the teeth. Orthodontists prefer using an orthodontic retainer for this purpose. Such a retainer is formed in part using the plaster mold impression of the teeth of the patients (step 235).

As described above, a conventional retainer uses a round or flat stainless steel wire that is in contact with the front teeth and is attached to the molar clasps on the teeth that are in the back of the mouth. Such a retainer is illustrated in FIG. 2. The palate of the mouth is covered with an acrylic wafer of plastic to which the molar clasps are attached. The flat, clear strap of polymer described above is used to replace the stainless steel wire that is currently being used in retainers.

Attachment of the Labial Bow to the Orthodontic Retainer

Two adjusting loops are made in the wire extensions of the coil spring joint. Pliers are used to hold the coil spring joint while the wire next to the joint is being bent. The pliers should be used to hold the coil spring joint in a manner such that the joint will not be deformed. This assembly is mounted to the arch or dental retainer by soldering the wire extensions to the molar clasps (step 240). At this point in the process, when the retainer is placed on the plaster cast of the mount, the plastic strap is located approximately 2-6 mm away from the front teeth of the plaster cast of the mouth. To adjust the position of the plastic strap relative to the front teeth, the plastic strap is carefully heated with a heat gun at a temperature of approximately 500-600 degrees Fahrenheit (step 245). The nozzle of the heat gun should be kept about 1.5 inches away from the plastic to avoid overheating. The heat causes the plastic of the strap to shrink and thereby move the plastic strap back in the direction of and against the teeth of the mold, which will result in a better fit of the retainer to the patient's teeth. It was found that tweezers can be used to facilitate adapting the plastic to the teeth for a custom fit. The final result is a highly durable clear and stain resistant plastic labial wire that can be used in many orthodontic retainers.

While several particular forms of the invention have been illustrated and described, it will be apparent that various modifications and combinations of the invention detailed in the text and drawings can be made without departing from the spirit and scope of the invention. For example, references to materials of construction, methods of construction, specific dimensions, shapes, utilities or applications are also not intended to be limiting in any manner and other materials and dimensions could be substituted and remain within the spirit and scope of the invention. Accordingly, it is not intended that the invention be limited, except as by the appended claims.

What is claimed is:

1. A dentition retaining apparatus comprising:
   a joint between a holding member and a supporting member;
   the holding member formed of a highly oriented polymer and being configured to be placed against the front teeth of a patient, being elastically deformable, having a first portion with at least one flat surface and a second portion extending from the first portion, the second portion having a length with an outer diameter; and
   the joint comprising a coil extending from the supporting member and having an inner diameter that is less than the outer diameter of the second portion of the holding member and being placed around at least a portion of the second portion of the holding member whereby the coil compresses or is compressed against the second portion of the holding member to form the joint between the holding member and the supporting member.

2. The dentition retaining apparatus of claim 1, wherein the coil comprises at least approximately one-half of a revolution.

3. The dentition retaining apparatus of claim 1, wherein the coil comprises between approximately one-half of a revolution and thirty revolutions.

4. The dentition retaining apparatus of claim 1, wherein the coil comprises between approximately one-half of a revolution and three revolutions.

5. The dentition retaining apparatus of claim 4, wherein the coil comprises approximately one and one-half revolutions.

6. The dentition retaining apparatus of claim 1, wherein the inner diameter of the coil is less than the outer diameter of the second portion of the holding member prior to placing the coil around the second portion.

7. The dentition retaining apparatus of claim 1, wherein the inner diameter of the coil is the same as or greater than the outer diameter of the second portion of the holding member prior to placing the coil around the second portion.

8. The dentition retaining apparatus of claim 1, wherein the inner diameter of the coil is less than the outer diameter of the second portion of the holding member after placing the coil around the second portion.

9. The dentition retaining apparatus of claim 1, wherein the coil has a pitch angle between approximately 15 degrees and approximately 90 degrees.

10. The dentition retaining apparatus of claim 9, wherein the coil has a pitch angle between approximately 40 degrees and 50 degrees.

11. The dentition retaining apparatus of claim 1, wherein the coil has a spacing of between approximately 0 mm and 25 mm.

12. The dentition retaining apparatus of claim 11, wherein the coil has a spacing of between approximately 0 mm and 3 mm.

13. The dentition retaining apparatus of claim 1, wherein the coil is made of a wire having an outer diameter of between approximately 0.5 mm and approximately 3 mm.

14. The dentition retaining apparatus of claim 13, wherein the wire has an outer diameter of between approximately 0.8 mm and approximately 1.2 mm.

15. The dentition retaining apparatus of claim 1, wherein the joint has a length of between approximately 1 mm and 10 mm.

16. The dentition retaining apparatus of claim 15, wherein the length of the joint is between approximately 4 mm and 8 mm.

17. The dentition retaining apparatus of claim 1, wherein the supporting member comprises a metal or polymer material.

18. The dentition retaining apparatus of claim 1, wherein the dentition retaining apparatus comprises one or more of a retainer and a labial bow.

19. The dentition retaining apparatus of claim 1, wherein the joint is able to hold a static weight of more than about 9 kg to at least about 13 kg.

20. A process for forming a dentition retaining apparatus, the process comprising:
   a) providing a holding member, the holding member being configured to be placed against the front teeth of a patient, being elastically deformable, having a first portion with at least one flat surface and a second portion extending from the first portion, the second portion having a length with an outer diameter;
   b) providing a supporting member having a coil extending from the supporting member, the coil having an inner diameter that is less than, the same as, or greater than the outer diameter of the second portion of the holding member; and
   c) placing the coil around at least a portion of the second portion of the holding member to form a joint between the holding member and the supporting member, whereby the coil compresses or is compressed against the second portion of the holding member resulting in intertwining of the coil with the elastically deformable holding member to provide a holding ability of the supporting member to the holding member.

21. The process of claim 20, wherein the coil is compressed against the second portion of the holding member when the inner diameter of the coil is greater than the outer diameter of the second portion.

22. A labial bow comprising:
   a) a clear holding member configured to be positioned against the front teeth of a patient, the holding member being elastically deformable and having a middle portion with at least one flat surface and two side portions extending from the middle portions, the side portions being generally tubular in shape and having an outer diameter, wherein the holding member is formed of a highly oriented polymer; and
   b) a supporting member, the supporting member configured to be positioned against the side teeth of a patient, being formed of a metal and terminating in a coil at one end with the coil having an inner diameter that is less than the outer diameter of the end segment of the holding member and being placed around at least a portion of the end segment of the holding member whereby the coil compresses or is compressed against the end segment of the holding member to form a joint between the holding member and the supporting member.

23. The labial bow of claim 22, wherein the labial bow is mounted to a dental retainer arch to form a dental retainer.

24. A method of correcting the orientation of teeth, the method comprising:
providing a dentition retaining apparatus comprising a joint between a holding member and a supporting member;
the holding member formed of a highly oriented polymer and being configured to be placed against the front teeth of a patient, being elastically deformable, having a first portion with at least one flat surface and a second portion extending from the first portion, the second portion having a length with an outer diameter; and
the joint comprising a coil extending from the supporting member and having an inner diameter that is less than the outer diameter of the second portion of the holding member and being placed around at least a portion of the second portion of the holding member whereby the coil compresses or is compressed against the second portion of the holding member to form a joint between the holding member and the supporting member.

25. The method of claim 24, wherein the coil is crimped or compressed against the second portion of the holding member when the inner diameter of the coil is greater than the outer diameter of the second portion.

26. The method of claim 24, wherein the joint comprises an intertwining of the coil with the elastically deformable holding member to provide a holding ability of the supporting member to the holding member.

27. The dentition retaining apparatus of claim 1, wherein the joint comprises an intertwining of the coil with the elastically deformable holding member to provide a holding ability of the supporting member to the holding member.

28. The process for forming a dentition retaining apparatus of claim 20, wherein the joint comprises an intertwining of the coil with the elastically deformable holding member to provide a holding ability of the supporting member to the holding member.

\* \* \* \* \*